(12) United States Patent
Dall'Omo et al.

(10) Patent No.: US 11,867,678 B2
(45) Date of Patent: Jan. 9, 2024

(54) TEST DEVICE AND SYSTEM FOR A DETECTOR BASED ON THE DETECTION OF A GAS OR OF A GAS/PARTICLE MIXTURE

(71) Applicant: COMMISSARIAT A L'ENERGIE ATOMIQUE ET AUX ENERGIES ALTERNATIVES, Paris (FR)

(72) Inventors: Christophe Dall'Omo, Grenoble (FR); David Schatz, Is sur Tille (FR); Roland Pelisson, Grenoble (FR); Nicolas Deparis, Grenoble (FR); Norbert Daniele, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 17/351,186

(22) Filed: Jun. 17, 2021

(65) Prior Publication Data
US 2021/0396728 A1    Dec. 23, 2021

(30) Foreign Application Priority Data
Jun. 19, 2020 (FR) ...................................... 2006404

(51) Int. Cl.
*G01N 33/00* (2006.01)
*G01N 1/38* (2006.01)
(Continued)

(52) U.S. Cl.
CPC ............. *G01N 33/007* (2013.01); *G01N 1/38* (2013.01); *G01N 2021/5984* (2013.01); *G01N 2033/0072* (2013.01); *G08C 17/02* (2013.01)

(58) Field of Classification Search
CPC ....... G01N 2033/0072; G01N 33/0006; G01N 33/007; G01N 1/38; G01N 2021/7796;
(Continued)

(56) References Cited

U.S. PATENT DOCUMENTS

| | | | | |
|---|---|---|---|---|
| 4,882,576 A | * | 11/1989 | Boyd | ................. G01N 33/0006 422/83 |
| 2003/0126918 A1 | * | 7/2003 | Chuang | ............... B60C 23/0408 73/146 |

(Continued)

FOREIGN PATENT DOCUMENTS

| CN | 107911842 A | * | 4/2018 | ........... H04L 1/0006 |
|---|---|---|---|---|
| CN | 108932830 A | * | 12/2018 | |

(Continued)

*Primary Examiner* — John Fitzgerald
*Assistant Examiner* — Truong D Phan
(74) *Attorney, Agent, or Firm* — BakerHostetler (57) ABSTRACT

A test device for a detector for detecting gas or a gas/particle mixture, includes a joining means for joining the test device to the detector; a container configured so as to receive a gas or a test gas/particle mixture; a diffusion means associated with the container and designed to diffuse the gas or the test gas/particle mixture in the detector; an energy source; and a radio apparatus able to manage local radio communication in order to remotely trigger the diffusion of the gas or of the test gas/particle mixture in the diffusion means from a control means. A test system comprising at least one test device, at least one radio gateway, a control network comprising a control unit able to remotely control the test device and at least one communication link between the control unit and the radio gateway, said gateway being able to connect the radio apparatus and the control network.

21 Claims, 9 Drawing Sheets

(51) Int. Cl.
*G08C 17/02* (2006.01)
*G01N 21/59* (2006.01)

(58) Field of Classification Search
CPC .......... G01N 29/223; G01N 2201/021; G01N 2021/598; G01N 2021/5984; H01L 2224/05554; H01L 2224/49171; G08B 17/10; G08B 25/10; G08B 26/006; G08B 26/007; G08B 29/145; G08C 17/02; G10K 11/004
USPC ...................................................... 73/866.5
See application file for complete search history.

(56) References Cited

U.S. PATENT DOCUMENTS

| | | | | |
|---|---|---|---|---|
| 2004/0035179 | A1* | 2/2004 | Koch | G08B 29/145 374/2 |
| 2006/0156789 | A1* | 7/2006 | Frank | G01N 33/0006 73/1.06 |
| 2010/0260111 | A1* | 10/2010 | Sung | H04L 69/14 370/328 |
| 2012/0300348 | A1* | 11/2012 | Franks | H02H 7/263 361/42 |
| 2013/0334326 | A1* | 12/2013 | Shan | G08C 17/02 236/51 |
| 2015/0302727 | A1 | 10/2015 | Piccolo, III et al. | |
| 2017/0195953 | A1* | 7/2017 | Amorim de Faria Cardote | H04W 52/0212 |
| 2019/0066484 | A1* | 2/2019 | Park | H04W 4/90 |

FOREIGN PATENT DOCUMENTS

| | | | |
|---|---|---|---|
| CN | 208834461 U | * | 5/2019 |
| EP | 1 468 409 A1 | | 10/2004 |
| EP | 1 580 706 A1 | | 9/2005 |
| EP | 2 988 282 A1 | | 2/2016 |
| EP | 3 579 209 A1 | | 12/2019 |
| GB | 2 543 065 A | | 4/2017 |
| JP | 2019109674 A | * | 7/2019 |

* cited by examiner

TEST DEVICE AND SYSTEM FOR A DETECTOR BASED ON THE DETECTION OF A GAS OR OF A GAS/PARTICLE MIXTURE

CROSS-REFERENCE TO RELATED APPLICATIONS

This application claims priority to foreign French patent application No. FR 2006404, filed on Jun. 19, 2020, the disclosure of which is incorporated by reference in its entirety.

FIELD OF THE INVENTION

The present invention relates to a test device for a detector based on the detection of gas or of a gas/particle mixture, in particular for an automatic fire detector (referred to as "AFD") based on the detection of smoke. The test device according to the invention is designed to be joined to the detector, to be autonomous in terms of energy and to be able to manage radio communication in order to remotely trigger the diffusion of the test gas or of the test gas/particle mixture to the detector from a control means.

The invention also relates to a test system that comprises one or more test devices, a control network comprising a control means and at least one radio gateway connecting the one or more test devices and the control unit.

The invention also relates to a detector system comprising a test system and at least one detector.

BACKGROUND

The majority of tests on smoke detector-type automatic fire detectors are generally performed manually by an operator and aim to bring a test gas, and more precisely a test gas/particle mixture (smoke generally in aerosol form) as close as possible to the detector head, more often than not using a perch, while at the same time communicating, using a radio means available to the operator (VHF/UHF PMR radio), with a supervision system of the detector, and doing so in order to validate or not validate the test.

More complex Scorpion® test systems have been developed, in which a tester is mounted next to a smoke detector-type fire detector, the tester comprising a support rail that is attached to the fire detector to be tested or on the base of which said fire detector is mounted, a body containing an aerosol and a nozzle connected to the body, from which a jet of aerosol generated by the tester is directed at the detection head of the fire detector. The tester uses its own independent power supply and data cables and it uses a test control panel separate from any preinstalled wiring of the fire detection system and from the preinstalled control panel of the fire detection system. Multiple fire detectors are connected in wired form to a fixed control panel (controlling 1 to 8 heads), or to a portable control panel via a terminal (controlling 1 to 4 heads), the whole assembly also being wired. In both cases, it is necessary to have one tester cable per detector, and a cable is also limited to a length of 100 metres. Lastly, to perform a fire detector test, an operator has to visit the site of the fire detection system, put the system into test mode, and then introduce a power source to the test control panel of the Scorpion® system, and said operator thus has to face the fixed control panel or the portable control panel.

Although such a test system makes it possible to reach fire detectors that are located at a height and are difficult to reach and/or difficult to access, it is however necessary to fit each tester with wires. It is therefore relatively expensive to install due to the need to deploy specific control and power supply cables for the test system. The action distance is also limited to 100 metres. In addition, the tester requires the provision of a relatively large amount of energy during operation to generate the aerosol. Lastly, due to the size of the Scorpion® heads, the orientation of the tester affects the effectiveness of the tests that are performed, the tester being able to be inserted in position only along a certain axis (for example along a corridor), but the airflow at this location may oppose the passage of the aerosol to the detection component, thereby reducing the reliability of any test.

There are some systems, such as the system described in patent application EP1468409A1, comprising fire detectors, each one being equipped with an RFID electronic device containing information specific to the detector (identification number, date of the last test, result of the test, etc.) and a test device located on a perch of adjustable length, for example a telescopic perch, so as to be able to reach each of the detectors, and comprising readout means for reading the data from the RFID electronic device. The detectors and the test device may thus communicate through a short-range wireless system, but this is limited to the exchange of data. However, it is still necessary to have a perch so that the test device reaches each detector. The test therefore cannot be controlled remotely. Patent application EP2988282A1 also describes a fire detector in which there is installed an RFID chip that allows data to be communicated and transferred between the fire detector and a test tool for testing the detector, this time without a perch, but this is also limited to the exchange of data in close proximity. The test therefore cannot be controlled remotely.

There are some fire detection systems that integrate test means, called "self-test systems", as described in application US2015302727A1, which indicates that self-test systems do not always make it possible to completely validate the operation of fire detectors, notably when a path of a fire detector is obstructed, and which proposes a device for determining whether a path is obstructed. The proposed device comprises a light source for directing light into the paths and one or more sensors positioned in the detector so as to be able to analyse the light that is returned. The device thus makes it possible to detect obstructions in the paths by analysing the way in which light propagates through the paths. In the described fire detection system, each fire detector comprises, in a base unit, communication components allowing the detector to communicate with a control panel via a wired link (secure communication network). Patent application GB2543065A describes this obstruction problem, but rather addresses the drawbacks of the Scorpion® systems described above. It describes a test device for a fire detector comprising a liquid reservoir and an aerosol generator with vibrating meshes fluidically connected to the liquid reservoir in order to generate an aerosol from the liquid reservoir, arranged such that the aerosol, when it is generated, is directed at the detector element of a fire detector.

In these last two patent applications, the self-test function is controlled by the secure communication network of the fire detectors, and it is incorporated into the fire detectors, meaning that all of the fire detectors have to be changed in order to achieve this new function. This is therefore not a function that is easily added to fire detectors.

SUMMARY OF THE INVENTION

The invention aims to overcome the abovementioned drawbacks of the prior art.

More particularly, it aims to provide a universal test device for a fire detector, and more generally for any detector based on the detection of gas or of a gas/particle mixture, which is able to be easily adaptable to any existing and/or preinstalled detector, which is remotely controllable (notably at a distance of greater than 100 metres), this being highly sought-after for detectors that are located at a height, difficult to reach and/or difficult to access.

What is also sought is an autonomous test device that makes it possible to dispense with perches, nacelles or other means for getting close to the detector to be tested, and which makes it possible to dispense with significant amounts and lengths of cables.

What is also sought is a test system that has low energy consumption, that is fast to implement, and that is reliable.

What is also sought is a test that is easy to implement, and is able to be implemented notably without an operator.

A device for rectifying these drawbacks is a test device for a detector based on the detection of gas or of a gas/particle mixture, said device comprising:
 a joining means designed to join the test device to the detector to be tested;
 a container configured so as to receive a test gas or a test gas/particle mixture;
 a diffusion means associated with the container and designed to diffuse the test gas or the test gas/particle mixture in the detector;
 an energy source, for example an energy storage means, designed to give the test device autonomy in terms of energy; and
 a radio apparatus able to manage local radio communication, preferably bidirectional radio communication, in order at least to remotely trigger the diffusion of the test gas or of the test gas/particle mixture in the diffusion means, and thus in the detector, from a control means.

The radio communication may be established with a control network comprising a control means, specifically by way of at least one radio gateway.

The test device according to the invention may furthermore comprise one or more of the following embodiments, taken in isolation or in any technically feasible combinations.

According to one embodiment, the container is able to receive or is a test gas cartridge or a test gas/particle mixture cartridge.

According to one embodiment, the diffusion means comprises a diffuser configured so as to route the test gas or the test gas/particle mixture as close as possible to the gas inlet of the detector.

According to one embodiment, the diffusion means comprises an element able to interact with the joining means.

According to one embodiment, the test device furthermore comprises a remotely controllable actuator able to actuate the diffusion of the test gas or of the test gas/particle mixture in the diffusion means, and thus in the detector.

According to one embodiment, the joining means comprises at least one hooking finger whose first end has a hook shape able to interact with an indentation in the detector.

According to one embodiment, the joining means comprises a fastening clip able to surround the detector.

According to one particular embodiment, the joining means comprises an adjusting means for adjusting the relative position of the test device with respect to the detector.

According to one particular embodiment, the joining means furthermore comprises at least one end designed to adjust the clamping or the releasing of the fastening clip around the detector, said at least one end preferably being positioned in the axis of the centre of gravity of the test device.

The local radio communication is preferably in accordance with LoRa technology, and the radio apparatus comprises a component compatible with LoRa technology, with a communication protocol based on the LoRaWAN protocol.

The test device preferably comprises an accurate time base, for example a real-time clock (RTC).

The radio apparatus furthermore preferably comprises a standby and periodic waking means, the waking periodicity being adaptable. The standby duration may also be adaptable.

According to one particular embodiment, the standby and periodic waking means for the test device is integrated into a software layer built onto the LoRaWAN layer of the radio apparatus of the test device.

The invention also relates to a test system comprising at least one test device according to the invention, and furthermore comprising:
 at least one radio gateway, and
 a control network comprising a control unit able to remotely control the at least one test device and at least one network communication link between said control unit and said at least one radio gateway;
 the at least one radio gateway being able to connect the radio apparatus of at least one test device and the control network.

A radio gateway is understood to mean a device for connecting two communication networks of different types. According to the invention, the radio gateway makes it possible to connect the radio apparatus and the control network comprising the control means. In the present description, the term "gateway" denotes a radio gateway for short.

A radio apparatus contributes to forming a local radio network using one or more radio gateways. When there are multiple test devices, there are multiple radio apparatuses in the local radio network. The local radio network thus denotes the network formed by the one or more test devices and the one or more gateways.

The radio apparatus makes it possible to exchange information with the control network via a radio gateway, preferably bidirectionally.

The control network denotes the network formed by the one or more gateways and the control unit, with the communication link connecting them, and may comprise other elements inserted between the one or more gateways and the control unit.

The control network may comprise or consist of an IP computer network. It will be recalled that an IP computer network is a communication network using the Internet Protocol (or "IP"). In the present description, the term "IP network" or "IP computer network" denotes a computer network using the Internet Protocol for short. Likewise, an "IP link" or "IP communication link" or "communication link using IP" denotes a communication link using the Internet Protocol.

The control network preferably comprises a universal time broadcast server able to synchronize with a time base in the test device, so as to have a common time base.

The control unit is preferably able to give standby and wake instructions to the test device, the waking periodicity being adaptable. The standby duration is also adaptable. This makes it possible to improve the autonomy of the test device.

The control network may be an IP network, the control unit then comprising an IP layer, the control unit being for example a desktop computer, a laptop computer, a tablet, a smartphone, etc.

According to one embodiment, the at least one network communication link is fully wired.

According to one embodiment, the control network comprises a network server and a communication interface having a communication protocol compatible with the radio apparatus and the at least one radio gateway, generally an application server.

The local radio communication is preferably in accordance with LoRa technology, the radio apparatus of the test device comprises a component compatible with LoRa technology, with a communication protocol based on the LoRaWAN protocol, and the at least one radio gateway is a LoRaWAN gateway.

According to one particular embodiment, the control network comprises a network server and an application server.

According to one particular embodiment, the standby and periodic waking means for the test device is integrated into a software layer built onto the LoRaWAN layer of the radio apparatus of the test device and onto the application server.

According to one embodiment, the control network comprises multiple communication links comprising a wired portion connecting the at least one gateway, the network server and the application server, and a wireless portion, for example in Wi-Fi mode, connecting the application server and the control unit. The control network may be an IP network, and the network communication links may be IP communication links.

According to one embodiment, the control network comprises multiple communication links comprising at least one wired and/or wireless IP communication link between the at least one gateway, the network server and the application server and at least one LoRa radio communication link between the at least one gateway and the control unit, the control unit comprising a portable device equipped with a radio component compatible with LoRa technology.

The test device and the test system according to the invention may comprise any one of the features listed above, taken in isolation or in any technically feasible combinations with other features.

The control unit may be contained within or be associated with a supervision unit for supervising one or more detectors.

The invention also relates to a detection system comprising a test system according to the invention and a detector based on the detection of gas or of a gas/particle mixture.

According to one preferred embodiment, the detector is a fire detector based on smoke detection.

BRIEF DESCRIPTION OF THE DRAWINGS

Other features and advantages of the invention will become apparent through the following description given by way of non-limiting illustration, provided with reference to the appended figures, in which.

In all of these figures, identical references may denote identical or similar elements.

In addition, the various portions shown in the figures are not necessarily shown to a uniform scale in order to make the figures more legible.

DETAILED DESCRIPTION

In the remainder of the description, the term "test gas" is used indiscriminately to describe the following: a gas, a mixture of various gases or else a mixture of gases and particles, designed to test a detector based on the detection of gas or of a gas/particle mixture.

It is furthermore clarified that, when an element is described as being linked, connected, assembled or joined to another element, and unless indicated otherwise, it may be linked, connected, assembled or joined to the other element directly, or intermediate elements may be present.

The test device is furthermore described in the detailed description with reference to a smoke detector-type fire detector, which may be called "smoke detector", even though it may apply to any other detector based on the detection of gas or of a gas/particle mixture within the scope of the claims. The same applies to the test system and the detection system.

Figure 1A:
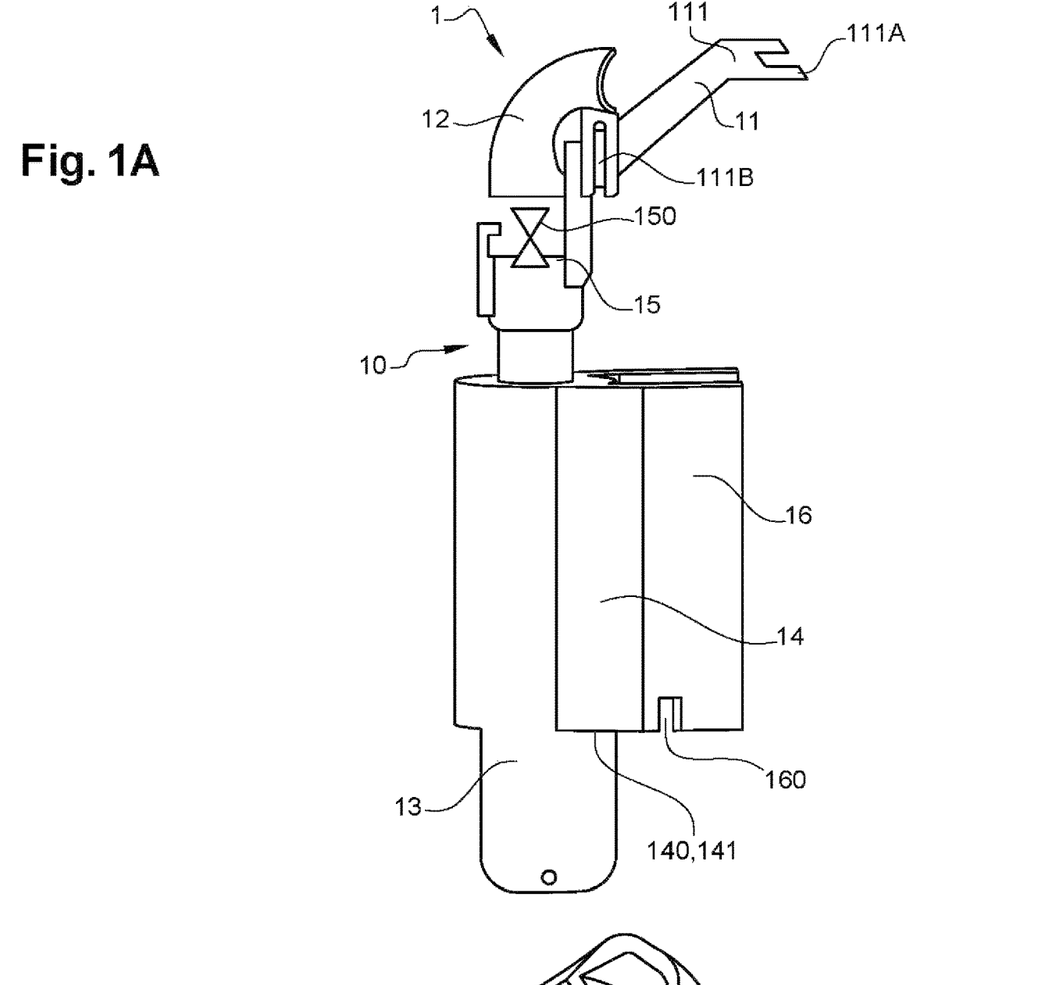
FIG. 1A and FIG. 1B show a first embodiment of a test device according to the invention.
Figure 1B:
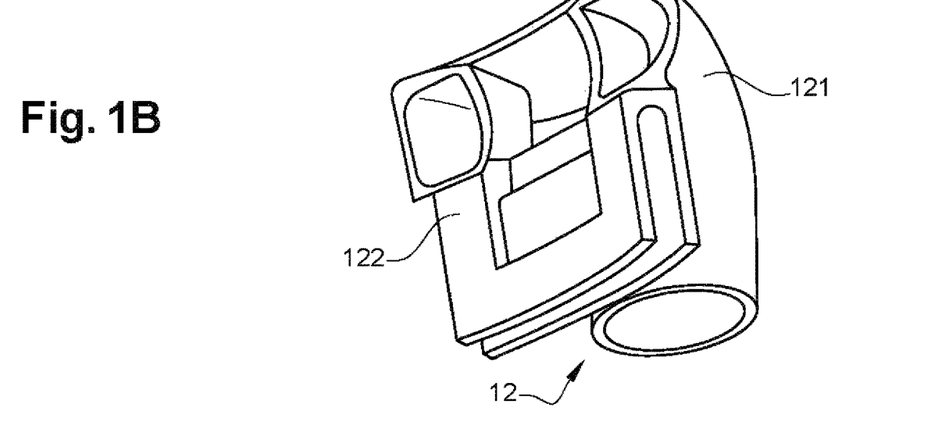

FIGS. 1A and 1B illustrate a first embodiment of a test device according to the invention that takes the form of a main body 10 connected to a joining means 11.

The main body may be made of plastic, of metal or any other suitable material, which is preferably lightweight, impact-resistant and durable over time. The height of the main body of the illustrated test device is 14 cm, its depth is around 4 cm and its width is around 5.5 cm.

The joining means illustrated in FIG. 1A comprises at least one hooking finger 111 whose first end 111A has a hook shape able to interact with an indentation in a detector (not shown in FIGS. 1A and 1B).

A smoke detector comprises gas inlet openings, for example in the form of fins, via which smoke is able to enter inside the detector so as to reach the detection components. These openings may form one or more indentations into which a hooking finger is able to be inserted.

Figure 2A:
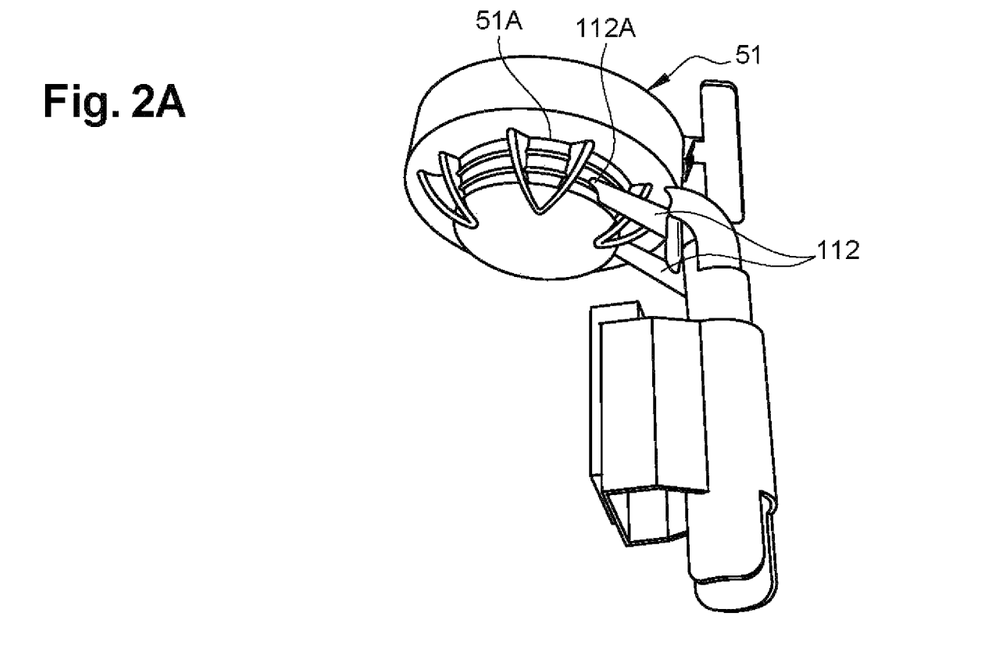
FIG. 2A shows a first variant of a test device according to the invention.
Figure 2B:
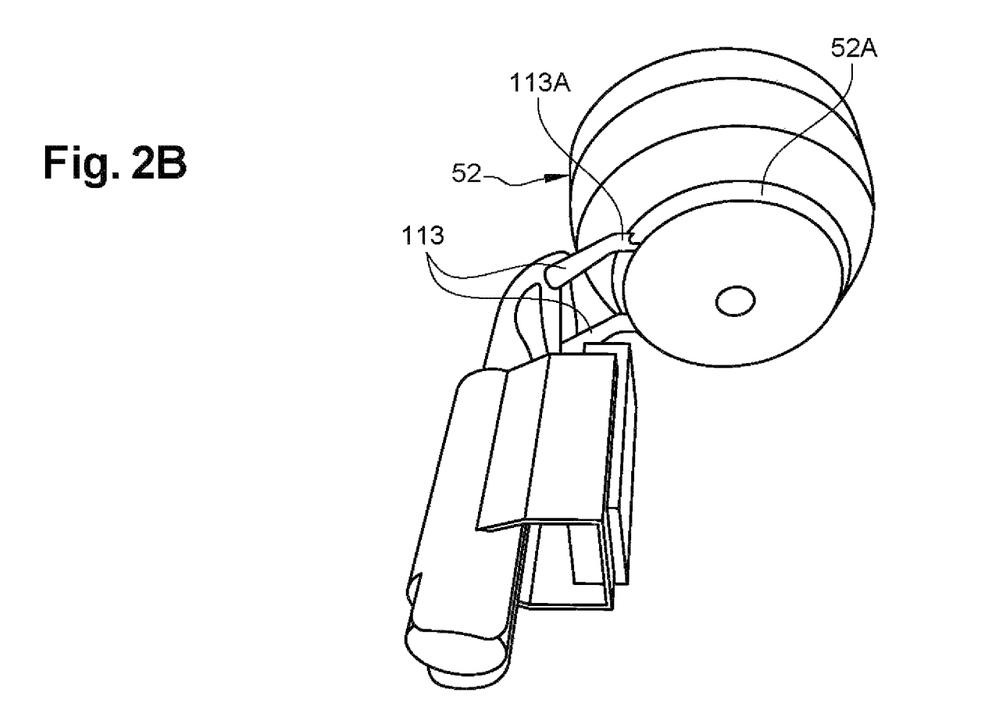
FIG. 2B shows a second variant of a test device according to the invention.

FIGS. 2A and 2B illustrate two variants of joining means in the form of hooking fingers with two different types of finger for adapting to two different types of detector.

A first variant, in FIG. 2A, shows two fingers 112 whose first ends 112A are designed to be inserted vertically between two vertical fins 51A of a first type of detector 51.

A second variant, in FIG. 2B, shows two fingers 113 whose first ends 113A are designed to be inserted horizontally between two horizontal fins 52A of a second type of detector 52.

In the two variants, this makes it possible to guarantee an optimum direction of diffusion of the test gas in the openings in the detector.

Joining means in the form of hooking fingers are easy to implement and may easily be adapted to different detectors, for example by adapting the shape of the one or more fingers, and notably by adapting the shape of the end of the one or more fingers that is intended to interact with the detector. The shapes that are described are non-limiting, and a person skilled in the art will know how to adapt them to other types of detector.

However, there are some detectors that do not comprise openings that are easy to hook onto one or more hooking fingers, or detectors for which joining to fingers might not be secure in the long term. The fingers may also have fragile areas, and may end up breaking after multiple hooking and unhooking operations. Lastly, such a hooking means may sometimes require excessively great accuracy for hooking the detector, and it is not always easy to perform this at a height.

Figure 3:
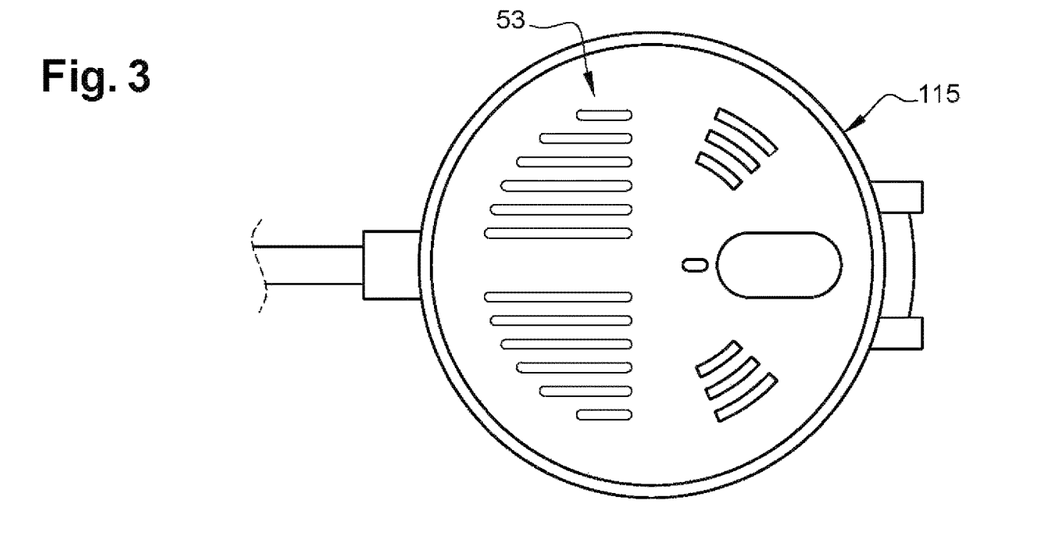
FIG. 3 shows a third variant of a test device according to the invention.

FIG. 3 illustrates a third variant showing a third type of detector 53, which does not comprise fins or openings that are easy to hook. The illustrated joining means 115 takes the form of a fastening clip, which is a clamping collar that encircles and surrounds the detector 53. Such a fastening clip is suitable here for any type of generally circular detector, but other clips may be adapted for shapes that are not completely circular. The first fastening clip may be made of plastic, of metal or of a mixed material.

The joining means described with reference to FIG. 3 is illustrated with the third type of detector 53, but it may be adapted to any type of detector. The other elements of the test device may be identical to those described further on in the present description.

Figure 4A:
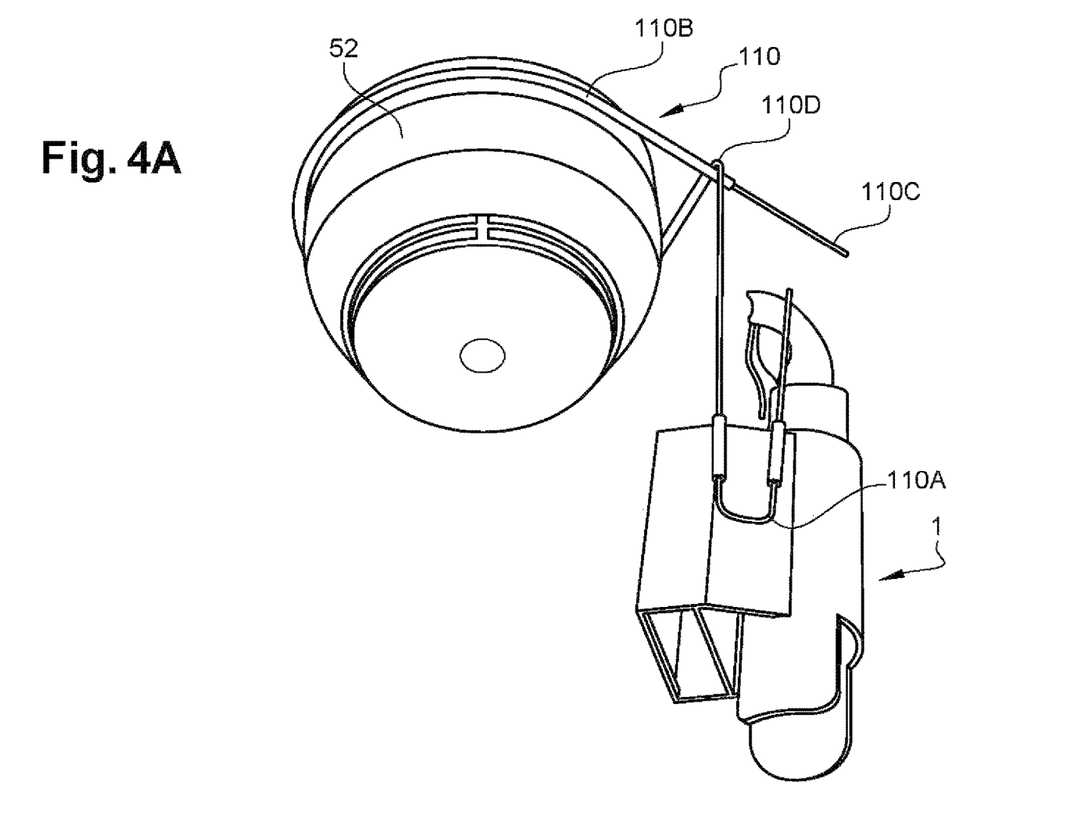
FIG. 4A and FIG. 4B show a fourth variant of a test device according to the invention.
Figure 4B:
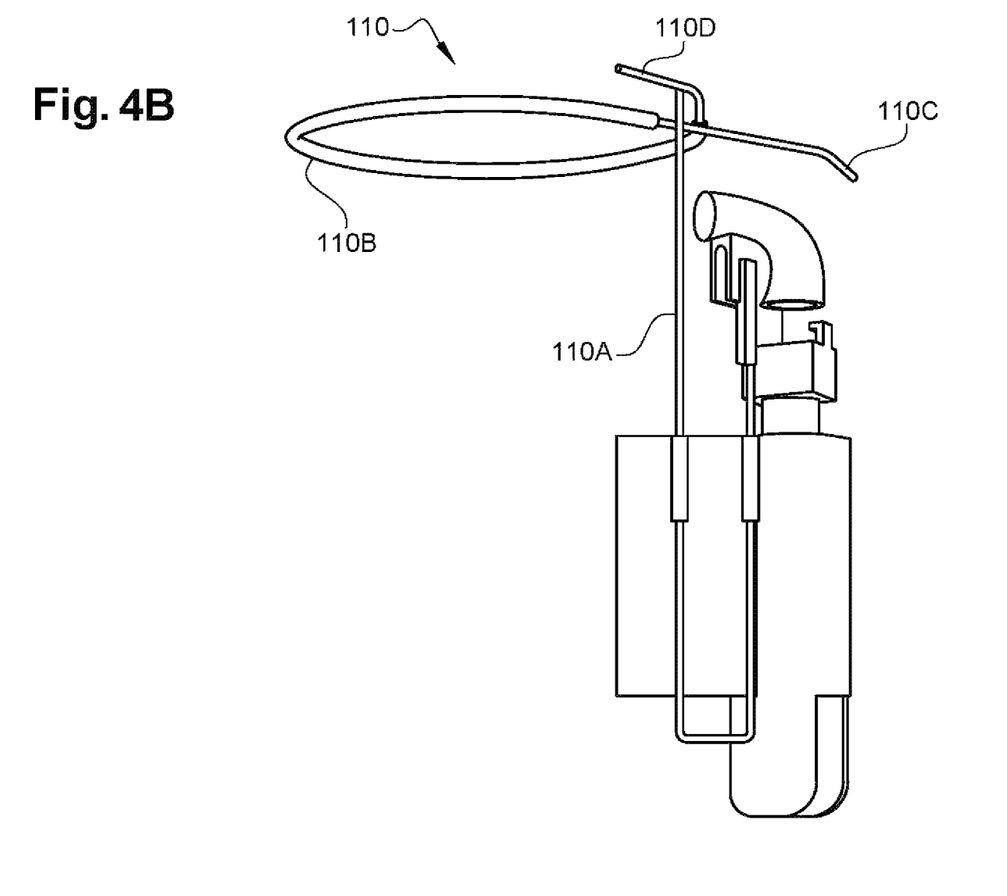

FIGS. 4A and 4B illustrate a fourth variant in which the joining means 110 takes the form of a metal wire having elastic (or return) properties, said metal wire being designed to allow the following functions:

positioning the test device on the metal wire at a defined height (preferably before it is assembled with the detector), through a first portion 110A of the metal wire forming a U-shaped loop: the U-shaped loop interacts with the main body of the test device so as to allow said test device to move in translation to a desired position of the diffusion means with respect to the detector;

fastening the test device around the detector through a second portion 110B of the wire forming a fastening clip (or clamping collar), said fastening clip being dimensioned so as to surround the detector: the clamping force of the fastening clip applied around the detector should be enough to clamp it while at the same time supporting the weight of the test device, while avoiding it sliding; the portion of the metal wire forming the fastening clip is preferably surrounded with a non-slip buffer material, such as a rubber, allowing the test device to be held around the detector (and avoiding sliding);

gripping the fastening clip 110B, so as to install it and remove it, via a first end 110C of the metal wire and a second end 110D of the metal wire that are easily able to be held, for example via a telescopic gripper equipped with pads or with flexible suction cups.

By performing substantially horizontal pressing on the tips of the two ends, it is possible to increase the diameter of the clip and notably to release the detector. By releasing the pressing on the two ends, it is possible to decrease the diameter of the clip and notably to clamp the detector.

The ends 110C and 110D are advantageously positioned in the axis of the centre of gravity of the test device. The test device is thereby naturally vertically positioned, throughout the holding process, by the suction cups until it is placed around the detector. Placement is thus greatly facilitated.

The first portion 110A of the metal wire forming a height adjustment system is connected to the second portion 110B of the metal wire by welding. As an alternative, the first portion 110A of the metal wire may be connected to the second portion 110B via the second end 110D by bending the metal wire at said second end (just one metal wire for forming the whole assembly).

This fastening clip is said to be "universal" (in the sense that it is not designed for a single type of detector), and it is advantageous in that it allows the test device to be adjusted in relation to the detector. Adjusting the height of the test device makes it possible to ensure that the diffuser is correctly arranged facing the gas inlet openings of the detector, for example facing the fins when the detector is equipped therewith. It is also advantageous through its ease of installation on the detector (it notably aligns automatically around this detector through the effect of gravity). It is also advantageous as it is able to be deposited easily: specifically, the suction cups or the pads do not need to be perfectly aligned in order to hold it.

The joining means described with reference to FIGS. 4A and 4B is illustrated with the second type of detector 52, but it may be adapted to any type of detector. The other elements of the test device may be identical to those described further on in the present description.

The upper end of the main body 10 is open, and it is profiled so as to form a diffusion means 12 comprising a diffuser 121 dimensioned so as to route the test gas as close as possible to the head of the detector.

It is clarified that the head of the detector denotes the portion of the detector that comprises the detection components.

The diffusion means 12 detailed in FIG. 1B comprises a first portion 121 forming the diffuser, which is in the form of an elbow-shaped duct connected to the test gas container 13 and dimensioned so as to route the test gas to the openings in the detector, such that the test gas is able to reach the head of the detector. The curved duct ensures that the test gas diffuses through a Venturi effect, by driving the test gas into the fins of the detector following a 90° deflection.

It is clarified that a diffuser is defined as being a static element for distributing a flow of gas.

The diffusion means 12 illustrated in FIG. 1B furthermore comprises a second portion 122 profiled so as to interact with the joining means, for example with the second end 111B of the finger 111, as illustrated in FIG. 1A. The joining means may be kept in place on the detector and the rest of the test device may be joined to or detached from said joining means, for example via this second portion 112 of the diffusion means 12, by moving the diffusion means in relation to the joining means, for example by sliding it so as to recover and easily reposition the diffusion means, for example during maintenance of the test device (notably for refilling the test gas cartridge).

If the joining means is held on the detector, the joining means preferably comprises at least three fastening points for fastening to the detector (for example three fingers or a fastening clip, or else any other suitable means) for preventing the diffuser from detaching in the event of vibrations or impacts (for example in the event of an earthquake).

A first compartment of the main body forms a container 13 dimensioned so as to receive a gas cartridge containing the test gas, the cartridge for example being a standard cartridge and being able to comprise a valve located at the top of the cartridge. As an alternative, the container may be the gas cartridge, and the test device comprises a means for holding said cartridge.

By way of illustration, it is possible to use a standard cartridge made of aluminium, with a capacity of 24 millilitres, a diameter of 25 millimetres and a length of 90 millimetres. The cartridge may be refillable or be a single-use cartridge.

The valve of the cartridge may be:
- a continuous (or vertical-action) valve: the test gas is released for as long as pressure is formed on the valve;
- a metering valve: the test gas may be released in a highly precise volume;
- a single-use valve that releases all of the test gas in the cartridge (lid pierced when installed).

For a smoke detector, the type of gas that is used is smoke for a smoke detector tester ("SDT" for smoke detector test), in the form of aerosol.

In the test device illustrated in FIG. 1, a second compartment 16 of the main body is designed to receive an energy source 160, which may be an energy storage means (for example one or more cells or a rechargeable battery or any other suitable means).

The test device illustrated in FIG. 1 furthermore comprises an actuator 150 able to actuate the introduction of the test gas from the gas cartridge into the diffuser (and thus to diffuse it in the detector). The actuator may be a solenoid valve or a mechanical actuator pressing on the valve of the cartridge.

The actuator fluidically connects the diffuser and the test gas cartridge. It may be arranged in a third compartment 15 of the main body located between the diffusion means and the test gas container. The actuator 150 is connected to the energy source 160 so as to be supplied with power and to an electronic board 140 so as to be driven. The electronic board is preferably dedicated to the actuator and should make it possible to ensure a current draw sufficient for it to operate correctly.

The actuator 150 may be a solenoid valve. The choice of a solenoid valve is preferred. Specifically, actuating the introduction of the test gas through a mechanical action on the valve of the cartridge requires significant effort in order to compress the spring of the valve (and this may also lack accuracy in terms of the amount of gas emitted, depending on the type of valve available on the cartridge).

A solenoid valve may comprise, on one of its ends, a female receptacle equipped with a toroidal gasket and designed to be connected to the male portion of the gas cartridge, and, on its other end, a lid for atomizing the gas (for example small hole in a metal sheet).

In the test device illustrated in FIG. 1A, the radio apparatus 140 is arranged in a fourth compartment 14 of the main body forming an electronic portion and dimensioned so as to receive electronic apparatuses. The fourth compartment may also receive the electronic board 141 of the actuator 150.

The local radio network between a test device and a gateway is preferably in accordance with the LoRaWAN radio protocol. LoRaWAN is the acronym for "Long-Range Wide-Area Network". LoRaWAN allows low-cost and low-consumption long-range communication. This may be a low-data-rate LoRaWAN communication protocol (0.3 to 50 kbps).

The radio apparatus 140 may then comprise an electronic board operating using LoRa radio technology, preferably operating around the frequency of 868 MHz (for Europe), 915 MHz (for the USA), or 780 MHz (for Asia), this frequency being a compromise between radio coverage and radio capacity. LoRa is the modulation technology linked to LoRaWAN. The electronic board may be an Internet of Things ("IoT") LoRa expansion board, for example a LoPy4 electronic board made by Pycom, having a LoRaWAN radio module, or else a radio board integrating a LoRa chip and developed specifically for applications targeted by the invention so as to improve efficiency, consumption, bulk and manufacturing cost. A radio antenna is connected to the LoRa expansion board via a connector or is printed directly onto the electronic board containing the radio module, so as to dispense with the cable and improve bulk and cost.

More generally, the radio apparatus 140 may comprise any component compatible with LoRa technology.

The electronic portion 14 may also comprise an accurate time base with very low energy consumption. This time base may for example be a real-time clock (or RTC).

The test device may thus be easily attached to a detector (using one or more hooking fingers, a fastening clip or using any other suitable means). The test device is given autonomy since it integrates an energy source, a test gas cartridge. The test device preferably comprises an actuator for actuating the release of the test gas from the cartridge to the diffuser, the actuator being supplied with power by the energy source, and an electronic device, such as an electronic board, for driving the actuator. Lastly, the test device comprises a radio apparatus, such as a LoRa radio module, allowing it to communicate remotely with a control unit arranged in a control network via a radio gateway (able to connect the local radio network and the control network, preferably bidirectionally). This communication is preferably performed at timestamped times whose time is referenced using a precise time base with low energy consumption.

The test device may thus actuate, upon remote command and via a radio protocol, a certain configurable quantity of test gas that is diffused into the gas inlet openings of a detector so as to trigger said detector (whose alarm may be shut off beforehand in order to perform the test) and to test the operation thereof remotely.

Figure 5:
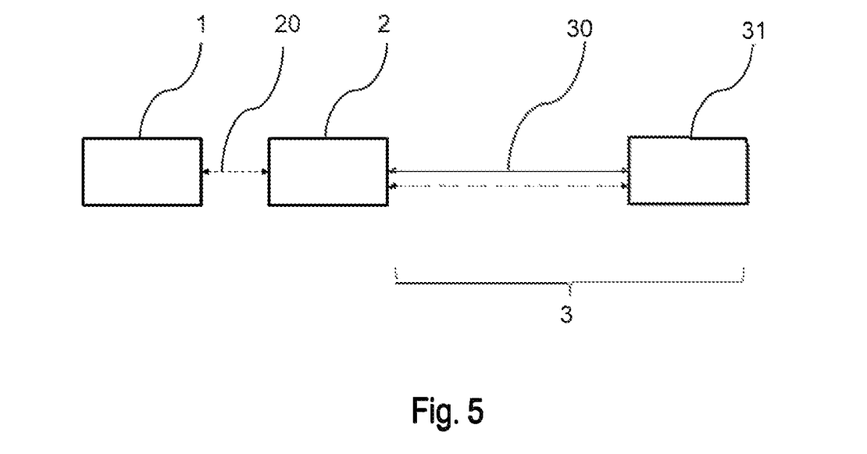
FIG. 5 shows a test system according to the invention.

FIG. 5 illustrates a test system according to the invention, comprising a test device 1, a radio gateway 2 and a control network 3.

A radio communication link 20 (represented by a dashed double-headed arrow) wirelessly connects the test device 1 and the gateway 2. The communication between the test device and the gateway is preferably bidirectional.

The control network 3 comprises at least a control unit 31 and a network communication link 30 between the control unit 31 and the radio gateway 2. The communication between the gateway and the control network is preferably bidirectional.

The network communication link 30 may be fully wired (represented by an unbroken double-headed arrow).

As an alternative, the network communication link 30 may be wireless (alternative represented by a mixed-line double-headed arrow). For example, the gateway may use a Wi-Fi terminal or a pre-existing cellular station and thus communicate wirelessly with the control unit.

As an alternative, with a radio control unit, the gateway may communicate with said such control unit in accordance with a radio protocol, for example the same radio protocol as for the radio communication between the test device and the gateway. In this case, the radio control unit is adapted for this radio protocol. This may be a remote controller with a radio component adapted to the radio protocol. Such a radio remote controller may be arranged so as to control the test device at a shorter distance, for example in the room or in the building where the detector is located. For example, if the radio control unit is a LoRaWAN remote controller, it is important to be able to get close to the test device in order to observe the behaviour of the detector when the test is triggered by the remote controller.

As another alternative, the network communication link may be mixed, that is to say with a wireless portion and a wired portion.

The test system may comprise multiple test devices associated with as many detectors, and also multiple radio gateways, and a control network with a control unit, the control network being connected to the gateways via wired, wireless or mixed communication links. A gateway may serve as a communication relay for multiple test devices, for example if the test devices are located within the radio coverage area of the gateway.

FIGS. 6A-6B, 7A-7B and 8A-8B illustrate second, third and fourth embodiments of a test system having a star-shaped network architecture, comprising multiple test devices 101, 102, 103, 104, 105, 106 each being equipped with a radio apparatus, and multiple gateways 21, 22, 23. The test devices and the gateways are distributed in three different areas (three different rooms P1, P2 and P3). The test system comprises a network 3 connected to each of the gateways.

In the same way as for FIG. 5, the radio communication links 20 are represented by dashed double-headed arrows.

Furthermore, a network communication link 30 is represented by an unbroken double-headed arrow (wired) or a mixed-line double-headed arrow (wireless or mixed) or else by a dashed double-headed arrow if this involves the same radio protocol as for the radio communication between the one or more test devices and the one or more gateways.

The radio apparatuses of the test devices preferably communicate bidirectionally with the radio gateways. The gateways likewise preferably communicate bidirectionally with the control network. Bidirectionality is advantageous since it makes it possible, in one direction, for a test device to receive the actuation command and, in the other direction, for the test device to acknowledge receipt of the command, to confirm that the test has been performed (for example if the test does not trigger the detector) and/or to provide information about the battery level and/or the gas cartridge level, etc.

Each test device and each gateway preferably has a unique identifier so as to improve the security of the test system, notably in order to authenticate the radio apparatuses. An encryption mechanism may also be provided using a digital key sharing mechanism.

Figure 6A:
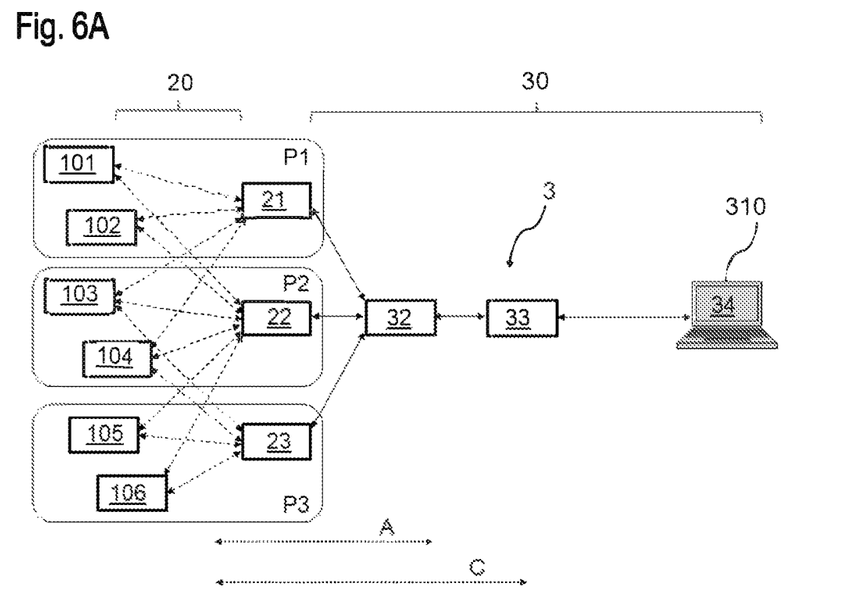
FIG. 6A and FIG. 6B show a first embodiment of a test system according to the invention.
Figure 7A:
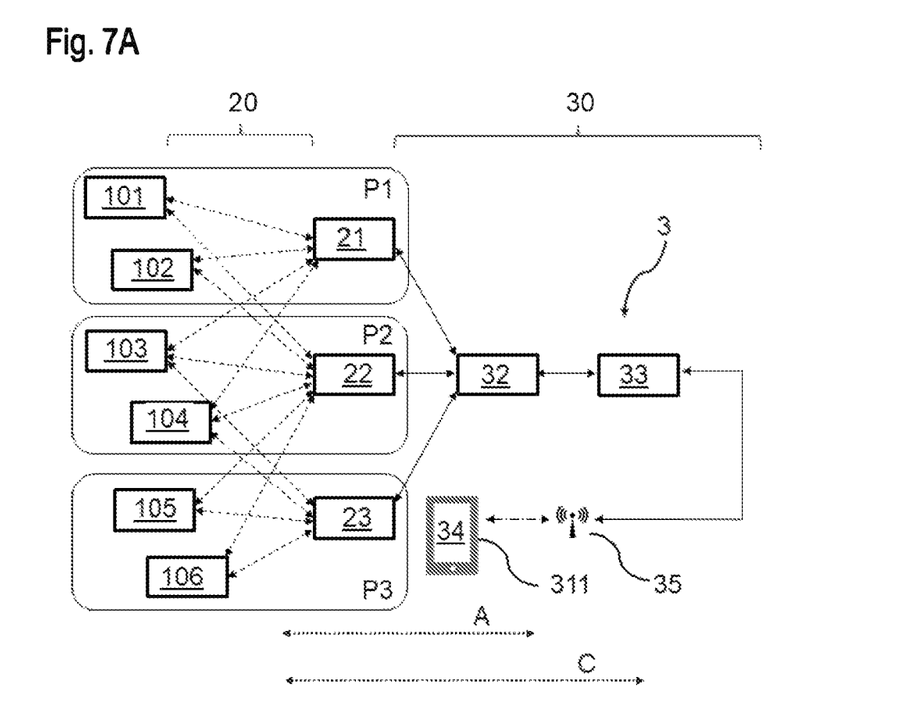
FIG. 7A and FIG. 7B show a second embodiment of a test system according to the invention.
Figure 8A:
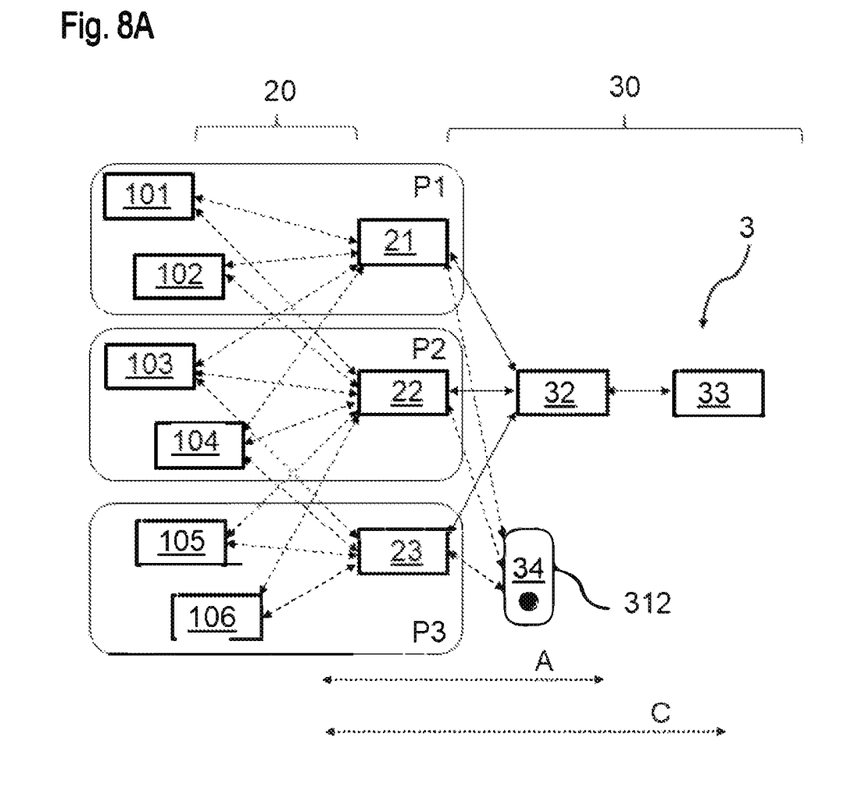
FIG. 8A and FIG. 8B show a third embodiment of a test system according to the invention.

According to the architectures illustrated in FIGS. 6A, 7A and 8A, the gateway 21 may serve as a communication relay for the test devices 101 and 102 in the same room P1, but also in the adjacent room P2. The gateway 23 may serve as a communication relay for the test devices 105 and 106 in the same room P3, but also in the adjacent room P2. The gateway 22 that is in the intermediate room P2 may serve as a communication relay for the six test devices that are in the three rooms.

Each gateway is connected to the control network via a wired link. As an alternative, a gateway may be connected to the control network via a Wi-Fi or cellular wireless link, or even via a mixed link.

In the systems illustrated in FIGS. 6A-6B, 7A-7B and 8A-8B, the local radio network between the test devices and the gateways is in accordance with LoRa radio technology, around the frequency of 868 MHz, with a LoRaWAN communication protocol.

The radio apparatus of each test device comprises at least one LoRaWAN radio module integrating a radio antenna so as to establish a LoRa radio link with one or more gateways, and the gateways are LoRaWAN gateways.

Some configuration parameters (among others) in LoRa technology are the spreading factor (or "SF"), the bandwidth (or "BW") and the channel coding rate ("coding rate" or "CR"). More particularly in a LoRaWAN architecture, each of these spreading factors SF, within a bandwidth BW of 125 kHz and coding rate of 4/5, have an associated data rate (or "DR") number ranging from 0 (the lowest data rate) to 5 (the highest data rate).

Radio apparatuses that use LoRa technologies are advantageous in that they are generally electronic apparatuses with low consumption, of small size and with low radio transmission power, and make it possible to communicate over long distances.

Using spread-spectrum LoRa technology, a LoRaWAN radio module is able to establish a bidirectional radio link with one or more different gateways. A LoRaWAN radio module has a unique identifier.

LoRaWAN gateways also all have a unique identifier and are able to simultaneously decode multiple frequency channels on multiple spreading factors SF.

The control network 3 that is shown comprises a control unit 310, 311, 312 and, in the direction from the gateway to the control unit:
- a network server 32;
- an application server 33; and
- an application or web server 34 implemented in the control unit.

The network communication links 30 may be TCP/IP links (transport layer/network layer), optionally with a protocol for securing exchanges over the Internet (typically SSL, TLS), arranged between the transport layer (TCP, etc.) and the application layer (HTTP, FTP, SMTP, MQTT, etc.).

Upon receiving a LoRaWAN frame from a radio module of a test device, a gateway transfers a packet over the IP link (using the MQTT protocol in TCP/IP in most cases), by adding radio information thereto: reference is then made to an "uplink". This information is intended for the network server 32. In the other direction, that is to say in what is called the "downlink", the information is transferred from the network server 32 to the radio module of a test device. Each LoRaWAN gateway thus has a "packet forwarder" function between a radio link using LoRa technology and an IP link, without implementing intelligence or specific filtering.

The main role of the network server 32 is to remove duplicates resulting from the uplink information. Specifically, since a packet from a radio apparatus may be received simultaneously by multiple gateways, the information is duplicated. For the downlink path, the network server selects a single gateway to transmit the packet. An authentication key A (for example of the type "NwkSKey") may be used by the network server to authenticate the radio apparatus.

The main roles of the application server 33 are to authenticate and decrypt the uplink information from the network server or the downlink information to the network server. The application server may additionally store information. The application server may have decryption keys C (for example of the type "AppSKey") shared with each of the radio apparatuses of the test devices.

Another optional function of the application server is that of decoding (respectively encoding) the radio frame.

The application or web server 34 is the last software block, at the end of the chain, of a standard LoRaWAN architecture. In the case of a detector test device according to the invention, the application makes it possible to perform encoding and decoding and to manage the control instructions and the information from the test devices or to the test devices. The communication interfaces of the application or web server generally use the HTTP protocol or the MQTT protocol, such that the graphical user interface is accessible from an Internet browser. This software block may easily be implemented in the control unit.

Figure 6B:
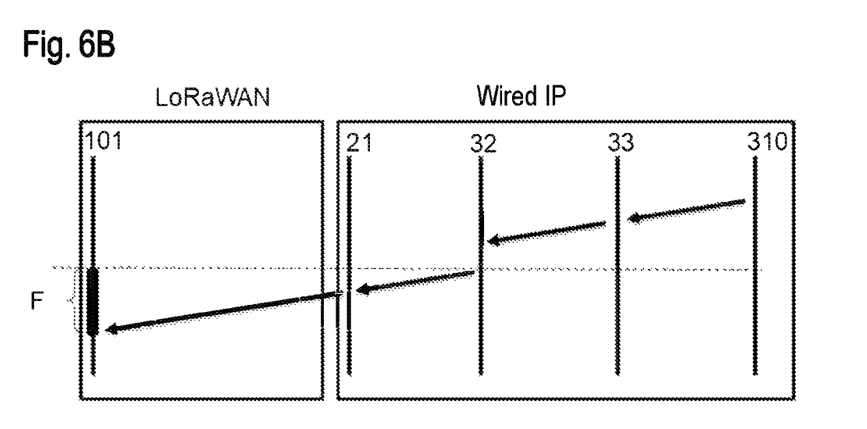

In the system shown in FIG. 6A, the control unit 310 is shown in the form of a laptop computer, but it may be a desktop computer, a tablet, a smartphone, and more generally any "client" device complying with the interfaces of the web server 34 (typically HTTP). The control unit is thus capable of remotely controlling any test device via its radio module. In this case, the control network 3 is an IP network and the network communication links 30 are wired IP links. FIG. 6B shows the routing of data (represented by arrows) between the control unit 310 and the test device 101 via the application server 33, the network server 32 and the gateway 21. The reference F represents the LoRaWAN listening window.

Figure 7B:
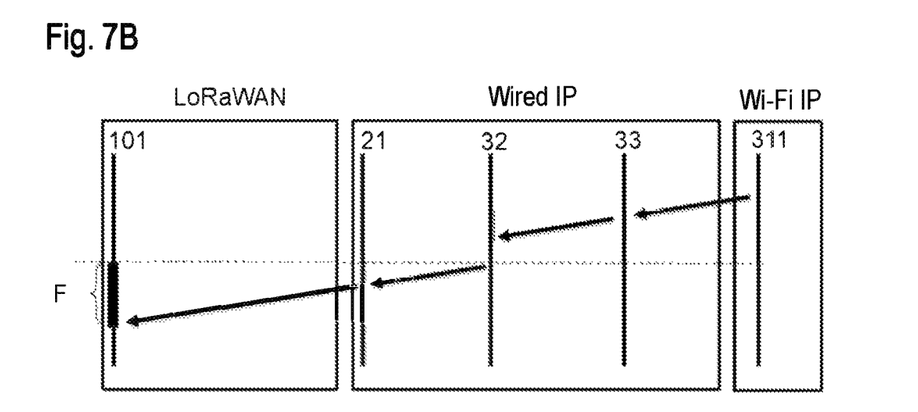

In the system shown in FIG. 7A, the control unit 311 is shown in the form of a tablet or of a smartphone. In this case, the control network 3 is an IP network and the communication links 30 comprise wired IP links between the gateways and the application server 33 and between the application server 33 and a Wi-Fi terminal 35, as well as a wireless link between the Wi-Fi terminal and the control unit 311. FIG. 7B shows the routing of data (represented by arrows) between the control unit 311 and the test device 101 via the application server 33, the network server 32 and the gateway 21. The reference F represents the LoRaWAN listening window.

Rather than being a Wi-Fi terminal, this may be a cellular station.

Figure 8B:
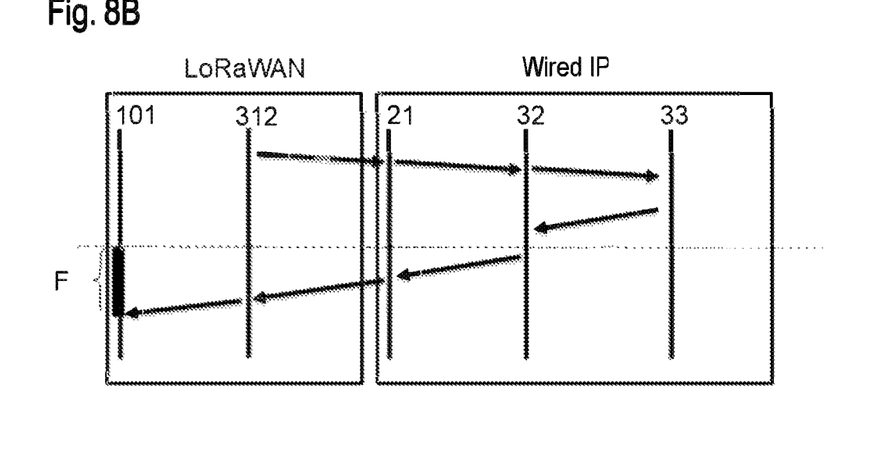

In the system shown in FIG. 8A, the control unit 312 is shown in the form of a LoRaWAN remote controller, which may more generally be a portable device equipped with a radio component compatible with the LoRaWAN protocol. In this case, the control network 3 comprises wired IP links between the gateways, the network server 32 and the application server 33 and LoRa radio links between the gateways and the LoRaWAN remote controller. FIG. 8B shows the routing of data (represented by arrows) between the control unit 312 and the test device 101 via the gateway 21, the network server 32 and the application server 33. The reference F represents the LoRaWAN listening window.

In the three configurations, the mechanism for triggering the test follows a client/server procedure. With a LoRaWAN radio link, the server is the application server, which may have two interfaces and two types of client:

a LoRaWAN interface through the network server, and the client is a dedicated radio device of LoRaWAN remote controller type;

an IP interface, for example of the type HTTP(s), MQTT(s), CoAP(s), and the client is any type of device complying with the interfaces of the web server, specifically in wired form (for example via an RJ45 cable) or in wireless form (Wi-Fi, cellular, etc.) or in mixed form.

Such a LoRaWAN architecture thus makes it possible to activate one or more detector test devices on command remotely, that is to say without having to visit the area under test. Control may be performed from a desktop computer, a laptop computer, a tablet and/or a smartphone, and more generally from any "client" device complying with the interfaces of the web server, or else via a LoRaWAN remote controller.

The frequency band of 868 MHz (for Europe) is well-suited to the field of the invention, since it allows a good compromise between the radio coverage area and the capacity of the test system (number of devices covered by the gateway) so as to cover a building.

The standard LoRaWAN communication protocol requires the use of classes (A, B and C). The main difference between these classes lies in the number of windows allocated by the radio apparatus for receiving messages sent by the control network. A distinction is thus drawn between:

Class A, which allows the transmission of an information packet followed by two listening windows; single opportunities for allowing the downlink transmission of information from the control unit to the radio apparatus. This class allows great autonomy in terms of electricity consumption of the test devices. The drawback is that the test devices transmit on a random basis (possibility of collision of data) with a short listening period (not much time to react in the control network). The responsiveness of the control network is therefore conditional on the transmission periodicity of the packets from the radio apparatuses. At a greater transmission frequency, this results in worse autonomy, so as to exhibit worse latency;

Class B, which allows the transmission of an information packet followed by multiple listening windows whose periodicity is optimized (for example every minute) in accordance with a compromise between latency and autonomy;

Class C, which allows the transmission of an information packet followed by at least one continuous listening window allowing a latency of virtually zero (very high responsiveness of the test devices, but worse autonomy).

As a first variant, the inventors propose a "TDMA" ("time-division multiple-access") class A that makes it possible to avoid the risks of collisions of radio packets on one and the same radio frequency channel. This makes it possible to dispense with class A random access operations and thus considerably improve quality of service. The principle is that of synchronously assigning the transmission times in terms of time and frequency in order to control these collisions. In this variant, the compromise between latency and consumption is optimized on the basis of the maximum latency requested by the operator and of test planning established beforehand using a dedicated algorithm.

Furthermore, in order to optimize the autonomy of the test device, the inventors have proposed a communication protocol based on standard LoRaWAN specifications by developing four operating states of the test devices:

What is called a "relaxed" state, in which the test device is in deep sleep mode (no transmission, no listening) for a period set by the control unit (for example 6 months). A "relaxed" state is preferably able to change only to a "transient" state. This improves the security of the test system, on the one hand, and its autonomy, on the other hand;

What is called a "transient" state, in which the test device is, preferably for a maximum duration of a few days (for example 5 days), in class A with a periodicity of several minutes to several hours. The transient state offers a potentially low quality of service, the quality depending on the number of test devices, and access to the communication medium (radio over the air) being purely random and the response time, defined as the time that has elapsed between the request from the control unit and the actuation of a test device, may not be compatible with the expectations of the operator during tests, but it has the function of allowing the operator to program the date and the time of the tests based on his planning. This programming is performed by switching the radio apparatus into a mode having lower responsiveness (sustained mode). A synchronization procedure between the absolute time of the server of the control network and the clocks of the radio devices is performed and confirmed by an acknowledgement message. A transient state may then change to a "relaxed" state or to a "sustained" state. In this transient state, the transmission periodicity of the radio packets from the test devices is random. The risk of collision is not controlled, and the quality of service decreases with the number of test devices and the transmission periodicity thereof;

What is called a "sustained" state, in which the device is either in permanent listening mode (class C) or listening with a latency time compatible with the needs of the operator, that is to say generally of the order of a minute (class A "TDMA"). This state should preferably last only for a few hours (for example 4 hours) due to the maximum electricity consumption, and has a good quality of service (maximum responsiveness of the order of a minute). This state makes it possible to change, at any time, to the "test" state or to change to the "transient" state if no test is performed at the end of the "sustained" state period, and makes it possible to offer the operator maximum responsiveness between the test request from the control unit and the actual actuation of the test on the test device. In this sustained state, the transmission periodicity of the radio packets from the test devices is synchronized with a single clock throughout the network (local radio network and control network). The assignment of the time and frequency windows is optimized by an algorithm that limits the risk of collision;

What is called a "test" state, in which the test device actuates the gas cartridge following a command launched by the control unit. This state lasts for at most 1 minute. It then changes directly to the "transient" state, awaiting reprogramming of the date of the next cycle.

Figure 9:
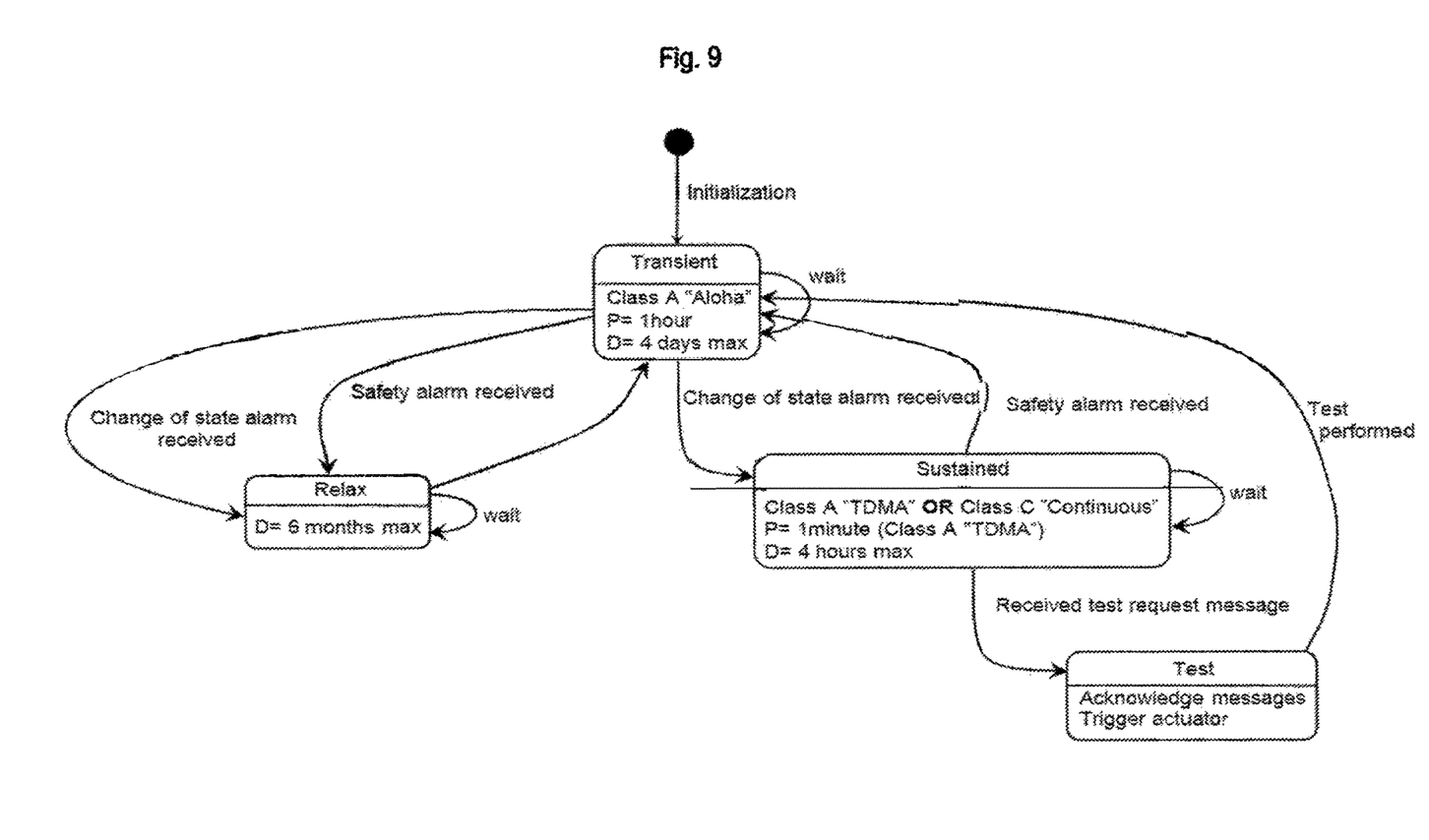
FIG. 9 shows a state graph illustrating one example of an operating protocol of a test system.

One example of a state graph given in FIG. 9 illustrates this operating protocol.

This protocol makes it possible to have a bidirectional link.

This developed protocol consists of a software layer built onto the LoRaWAN layer of the radio apparatus of the test device and onto the application server.

As an alternative to LoRa radio technology around the frequency of 868 MHz, it is possible to use another frequency band, for example the frequency of 915 MHz (for the USA) or of 780 MHz (for Asia), or else one of the following frequencies: 169 MHz, 433 MHz, 2.4 GHz, 5.8 GHz or any other suitable frequency band located between 9 kHz and 300 GHz.

As an alternative to LoRa radio technology, the radio network may be in accordance with another radio technology forming part of low-power wide-area networks, defined by the term "LPWAN".

As another alternative, the radio network may be in accordance with other technologies, such as the Zigbee standard (IEEE 802.15.4), Bluetooth™ Bluetooth™ Low Energy, which are wireless personal area networks ("WPAN").

A person skilled in the art will know how to adapt the control network depending on the radio technology that is adopted, depending on the type of control unit that is desired (desktop computer, laptop computer, a tablet, a smartphone, supervisor, radio remote controller, etc.) and depending on the interfaces and communication media desired in the control network.

The test system according to the invention may easily be integrated into an existing detection system. For example, an existing detection system consists of fire detectors whose information is fed back in wired form to a supervision system, generally via a control and/or signalling apparatus that communicates with safety means, for example in order to activate heat and smoke vents and/or to allow people to be evacuated by way of acoustic alarms or indicator lights. The test system according to the invention may communicate with the supervision system by way of the one or more gateways, and all of the elements of the existing detection system may be retained and operate in the same way. The control unit of the test system may be contained within or be associated with the supervision system (the application may for example be integrated into the supervision system in order to remotely control the various test devices).

Unless stated otherwise or obvious, the various embodiments and implementation variants that are presented may be combined with one another.

In addition, the present invention is not limited to the embodiments described above but rather extends to any embodiment that comes within the scope of the claims.

The invention claimed is:

1. A test device for a detector based on the detection of gas or of a gas and particle mixture, the device comprising:
a joining means designed to join the test device to the detector to be tested, the joining means comprising a fastening clip able to surround the detector and at least one end designed to adjust the clamping or the releasing of the fastening clip around the detector;
a container configured so as to receive at least one test gas or at least one test gas and particle mixture;
a diffusion means associated with the container and designed to diffuse the test gas or the test gas and particle mixture in the detector;
an energy source comprising an energy storage means designed to give the test device autonomy in terms of energy; and
a radio apparatus able to manage local radio communication comprising bidirectional radio communication, in order at least to remotely trigger the diffusion of the test gas or of the test gas and particle mixture in the diffusion means, and thus in the detector, from a control means,
wherein the joining means comprises a height adjustment portion configured for adjustably positioning the diffusion means with respect to the detector.

2. The test device according to claim 1, the container being able to receive or being a test gas cartridge or a test gas and particle mixture cartridge.

3. The test device according to claim 1, the diffusion means comprising a diffuser configured so as to route the test gas or the test gas and particle mixture as close as possible to the gas inlet of the detector.

4. The test device according to claim 1, the diffusion means comprising an element able to interact with the joining means.

5. The test device according to claim 1, furthermore comprising a remotely controllable actuator able to actuate the diffusion of the test gas or of the test gas and particle mixture in the diffusion means, and thus in the detector.

6. The test device according to claim 1, the joining means comprising at least one hooking finger whose first end has a hook shape able to interact with an indentation in the detector.

7. The test device according to claim 1, said at least one end of the joining means being positioned in the axis of the centre of gravity of the test device.

8. The test device according to claim 1, the joining means furthermore comprising an adjusting means for adjusting the relative position of the test device with respect to the detector.

9. The test device according to claim 1, comprising an accurate time base comprising a real-time clock, and a standby and periodic waking means for the test device, the waking periodicity being adaptable.

10. The test device according to claim 1, the local radio communication being in accordance with LoRa technology, the radio apparatus comprising a component compatible with LoRa technology, with a communication protocol based on the LoRaWAN protocol.

11. The test device according to claim 10 comprising an accurate time base comprising a real-time clock, and a standby and periodic waking means for the test device, the waking periodicity being adaptable, the standby and periodic waking means for the test device being integrated into a software layer built onto the LoRaWAN layer of the radio apparatus of the test device.

12. A test system for at least one detector based on the detection of gas or of a gas and particle mixture, said test system comprising at least one test device chosen in accordance with claim 1 and furthermore comprising:
at least one radio gateway, and
a control network comprising a control unit able to remotely control the at least one test device and at least one network communication link between said control unit and said at least one radio gateway;
the at least one radio gateway being able to connect the radio apparatus of the test device and the control network.

13. The test system according to claim 12, comprising a test device comprising an accurate time base comprising a real-time clock, and a standby and periodic waking means for the test device, the waking periodicity being adaptable, the control network comprising a universal time broadcast server able to synchronize with the time base of the test device, the control unit being able to give standby and wake instructions to the test device.

14. The test system according to claim 12, the control network being an IP network, the control unit comprising an IP layer, the control unit comprising a desktop computer, a laptop computer, a tablet or a smartphone.

15. The test system according to claim 12, the at least one network communication link being fully wired.

16. The test system according to claim 12, the local radio communication being in accordance with LoRa technology, the radio apparatus of the test device comprising a component compatible with LoRa technology, with a communication protocol based on the LoRaWAN protocol and the at least one radio gateway being a LoRaWAN gateway.

17. The test system according to claim 16, the control network furthermore comprising a network server and an application server.

18. The test system according to claim 17 comprising a test device comprising an accurate time base comprising a real-time clock, and a standby and periodic waking means for the test device, the waking periodicity being adaptable, the control network comprising a universal time broadcast server able to synchronize with the time base of the test device, the control unit being able to give standby and wake instructions to the test device, the standby and periodic waking means for the test device being integrated into a software layer built onto the LoRaWAN layer of the radio apparatus of said test device and onto the application server.

19. The test system according to claim 17, the control network comprising multiple communication links comprising a wired portion connecting the at least one gateway, the network server and the application server, and a wireless portion in Wi-Fi mode, connecting the application server and the control unit, at least one of the communication links being able to be IP communication links.

20. The test system according to claim 17, the control network comprising multiple communication links comprising at least one wired and/or wireless IP communication link between the at least one gateway, the network server and the application server and at least one LoRa radio communication link between the at least one gateway and the control unit, the control unit comprising a portable device equipped with a radio component compatible with LoRa technology.

21. A detection system comprising a test system according to claim 12 and a detector based on the detection of gas or of a gas and particle mixture the detector comprising a fire detector based on smoke detection.

* * * * *